US006491888B2

(12) United States Patent
Bell et al.

(10) Patent No.: US 6,491,888 B2
(45) Date of Patent: Dec. 10, 2002

(54) PH CONTROL METHOD OF REDUCING NITROGEN OXIDES EMISSION

(75) Inventors: Peter Simpson Bell, Glasgow (GB); Eric Nicholas Coker, Albuquerque, NM (US); Karen Small, West Lothian (GB)

(73) Assignee: BP Chemicals Limited, London (GB)

( * ) Notice: Subject to any disclaimer, the term of this patent is extended or adjusted under 35 U.S.C. 154(b) by 19 days.

(21) Appl. No.: 09/842,669

(22) Filed: Apr. 27, 2001

(65) Prior Publication Data
US 2002/0039551 A1 Apr. 4, 2002

Related U.S. Application Data

(63) Continuation of application No. PCT/GB99/03451, filed on Oct. 19, 1999.

(30) Foreign Application Priority Data
Oct. 29, 1999 (GB) .............................................. 9823726

(51) Int. Cl.7 .......................... B01D 53/72; C07C 7/11; C01F 1/00
(52) U.S. Cl. .................... 423/245.2; 585/809; 585/810; 585/843; 585/844; 423/345
(58) Field of Search .......................... 423/245.1, 245.2, 423/395; 585/809, 810, 843, 844

(56) References Cited

U.S. PATENT DOCUMENTS

| 2,077,041 | A | * | 4/1937 | Davis et al. ................ 585/809 |
| 2,463,482 | A | * | 3/1949 | Francis ....................... 585/809 |
| 2,498,204 | A | * | 2/1950 | Francis ....................... 585/809 |
| 2,673,225 | A | * | 3/1954 | Francis ....................... 585/809 |
| 3,395,192 | A | * | 7/1968 | Long .......................... 585/820 |
| 4,136,157 | A | * | 1/1979 | Asai et al. .................. 423/395 |
| 4,174,353 | A |   | 11/1979 | Marcinkowsky et al. ... 585/835 |

FOREIGN PATENT DOCUMENTS

| GB | 621873 |   | 4/1949 |
| GB | 1071373 | * | 6/1964 |
| WO | WO98/25871 |   | 6/1998 |

* cited by examiner

Primary Examiner—Wayne A. Langel
Assistant Examiner—Maribel Medina
(74) Attorney, Agent, or Firm—Finnegan, Henderson, Farabow, Garrett and Dunner, L.L.P.

(57) ABSTRACT

The invention relates to a process for the selective recovery of olefins from a mixture of gases by: a) bringing a gaseous mixture having olefins and hydrogen into contact with silver nitrate solution whereby the olefins are absorbed into the silver nitrate solution as a complex; b) separating the solution having complexed olefins from the non-absorbed gases; c) depressurising and heating the olefin complex solution from (b) so as to release the olefins from the complex and regenerate the silver nitrate solution; d) passing the regenerated silver nitrate solution through a bed containing silver oxide so as to maintain the pH value of the silver nitrate at between 3 and 6; and e) recycling the silver nitrate solution regenerated in (d) to step (a).

17 Claims, No Drawings

PH CONTROL METHOD OF REDUCING NITROGEN OXIDES EMISSION

This application is a continuation of international application number PCT/GB99/03451, filed Oct. 19, 1999.

This invention relates to a method of reducing nitrogen oxide emissions in processes involving selective olefin recovery from a mixture of gases generated in petrochemical processing.

In petrochemical processing such as eg an ethylene cracker, olefins are made by steam cracking hydrocarbon feedstocks. Such a process results in the formation of a mixture of olefins and paraffins such as eg ethylene, ethane, propylene and propane and is contaminated further with by-products which include hydrogen, diolefins and acetylenic compounds. Thus, the so-called 'Selective Olefin Recovery' (hereafter "SOR") processes have been devised to selectively recover olefins such as ethylene and propylene from the steam cracked products. The SOR process is based on the formation of a complex between the desired olefins and silver ions at relatively high gas pressures and relatively low temperatures. This complex formation is reversible in that when the pressure is reduced and the temperature is increased, the complex breaks down into the component olefin and silver ions. The SOR process is normally carried out by contacting the mixture of gases from the cracking process containing the olefins with an aqueous solution of silver nitrate (e.g. 2–6 M silver nitrate) in a vertical absorption tower at about 7 to 24 barg at and at 10–40° C. solution inlet temperature. A solution rich in the complex is withdrawn from the bottom of the absorption tower and fed into a lower pressure vessel which is maintained at a relatively higher temperature (e.g 60–110° C.) where the complex is broken down and the complexed olefin released and recovered. The remaining solution lean in olefins is cooled and recycled back to the absorption tower. A known SOR process is described in WO 98/25871.

It is well known, however, that the SOR process involving the use of silver nitrate solution is not straightforward. For instance, it is also known that hydrogen can lead to the decomposition of silver salt solutions to produce elemental silver. The high sensitivity of the silver nitrate solution to low levels of hydrogen has been established experimentally. Silver nitrate solution has been shown to remove free hydrogen down to levels of less than 10 ppm by bubbling gases containing various levels of hydrogen through silver nitrate solutions in glassware. The lowest concentration of hydrogen used corresponded to 10 ppm at 9 barg pressure. The reaction between hydrogen and silver nitrate can be represented by the following equation:

$$H_2 + 2AgNO_3 \leftrightarrow 2Ag + 2HNO_3 \tag{I}$$

Thus, it is clear that this reaction in which nitric acid is generated will lead to an increase in the acidity of the solution. For instance, the pH value of the silver nitrate solution continuously falls from the initial value of 4.5 to about 3.5 in about 2–3 weeks in a pilot reactor. Moreover, the precipitation of silver from the silver nitrate solution means that the silver nitrate solution becomes depleted in the silver ions necessary to complex the desired olefins, reducing the efficiency of the SOR process. Moreover, traces of methyl acetylene and acetylene in the gaseous cracked products fed to the absorber will also react with the silver nitrate solution to increase the acidity.

We have found that the above chemical reaction with hydrogen reaches equilibrium provided it is operated at a sufficiently high concentration of $HNO_3$, thereby preventing the deposition of silver. However, in order to achieve the desired concentration of acid, an increased level of nitric acid has to be used which in turn leads to an increase in the evolution of undesirable oxides of nitrogen (hereafter "$NO_x$") in the olefin product gas. For instance, the level of acidity required to prevent silver deposition was determined to be of the order of 20 wt % by determining the level of nitric acid required to redissolve precipitated silver. At this acidity level, the $NO_x$ impurity level is above the permitted limit of 1 ppm for $NO_x$ in eg the ethylene product. As a rough guide, the relative concentrations of $NO_x$ in a given silver nitrate solution can be summarised as follows:

| pH of 5 Molar Silver Nitrate Solution | $NO_x$ Level in Absorber Offgas (@ 30° C.) | $NO_x$ Level in Product Offgas (@ 90° C.) |
|---|---|---|
| 4.0 | 2 parts per billion | 4 parts per billion |
| 1.0 | 2 parts per billion | 1333 parts per billion |

It has now been found that the problem of controlling the pH of the silver nitrate solution in order to minimise $NO_x$ emissions can be reduced or eliminated by contacting the silver nitrate solution with silver oxide. This not only neutralises the acidity of the silver nitrate solution, but also replaces the silver ions lost by silver deposition by producing silver nitrate as a salt of neutralisation.

Accordingly, the present invention is a process for the selective recovery of a olefins from a mixture of gases, said process comprising:

a. bringing a gaseous mixture comprising olefins and hydrogen into contact with silver nitrate solution whereby the olefins are absorbed into the silver nitrate solution as a complex;

b. separating the solution comprising the complexed olefins from the non-absorbed gases;

C. depressurising and heating the olefin complex solution from (b) so as to release the olefins from the complex and regenerate the silver nitrate solution;

d. passing said regenerated silver nitrate solution through a bed comprising silver oxide so as to maintain the pH value of the silver nitrate at between 3 and 6; and e. recycling the silver nitrate solution regenerated in (d) to step (a).

The reaction of step a) may be carried out in an absorption tower. Under the reaction conditions which are usually of relatively high pressure and relatively low temperature, the olefins are absorbed into the silver nitrate solution as a complex. The hydrogen present in the gaseous mixture also reacts with silver nitrate to produce silver metal and nitric acid, which lowers the pH of the resulting solution.

Step a) may be carried out at pressures of about 5 to 40 barg, preferably, 7 to 24 barg.

Step a) may be carried out at temperatures of about 5 to 50° C., preferably, 15–30° C.

Preferably, the silver nitrate solution employed has a concentration of 1 to 10 M, preferably, 2 to 6 M, for example 5 M.

In step b), the solution comprising the complexed olefins is separated from the non-absorbed gases, and then depressurised and heated in step c). Step c) releases the olefins from the complex, and regenerates the silver nitrate solution. The regenerated silver nitrate solution is of an increased acidity compared with the original silver nitrate solution, and contains particulate silver as a result of the reaction between silver nitrate and hydrogen. The high concentrations of acid may result in high $NO_x$ values, and furthermore the formation of silver metal depletes the concentration of silver ions in the regenerated solution, thereby reducing its ability to complex olefins. As will be explained below, these difficulties may be alleviated by the use of silver oxide.

Optionally, the particulate silver suspended in the regenerated silver nitrate solution may be recovered by passing the regenerated silver nitrate solution through a filtering aid which is capable of retaining the particulate silver. This step is preferably carried out before passing the regenerated silver nitrate solution through a bed comprising silver oxide (i.e. step d). It is possible, however, for such a filtering step to be carried out at any point during the process of the present invention.

In step d), the regenerated silver nitrate solution is passed through a bed comprising silver oxide. The silver oxide neutralises the acidity of the silver nitrate solution by a reaction represented by the following equations (IIA and IIB):

$$Ag_2O+H_2O \rightarrow 2AgOH$$

$$AgOH+HNO_3 \rightarrow AgNO_3+H_2O$$

The reaction not only neutralises the nitric acid, but also produces silver nitrate. This silver nitrate is a source of silver ions which can be used to replace the silver ions lost, for example, in the reaction between hydrogen and silver nitrate. The treated silver nitrate solution from step d) can then be recycled to step a).

The process of the present invention is particularly suitable for selective recovery of olefins such as ethylene and propylene from petrochemical streams which have been subjected to steam cracking. The process of the present invention may enable the crude products of steam cracking to be processed for the recovery of olefins without any additional separation procedures to render such crude products completely free of compounds such as hydrogen, acetylenic compounds or the like. In operating this process, however, it may be desirable to remove acetylenic compounds before the main feedstream comprising the olefins and the other gases are fed to the absorption tower. This may be done by passing the feedstream through a guard bed comprising means (eg a source of silver ions) capable of forming an acetylide or acetylene complex with the acetylene and methyl acetylene present therein. A suitable example of such a guard bed having a source of silver ions is a commercially available silver-ion exchanged zeolite 13 X. By passing the feedstream through such a zeolite, substantially all of the acetylenic compounds may be removed from the feedstream. Alternatively, the feedstream can be fed directly into an absorption tower and the amount of acetylides formed in the silver nitrate solution can be monitored continuously to ensure that before they reach unacceptable levels, a suitable amount of these acetylides is removed A suitable method for removing acetylenes from a hydrocarbon stream is described in WO 98/25871. This method employs a selective hydrogenation step to reduce the concentration of acetylenes and dienes in the stream to ppm levels.

The aforementioned methods, however, do not remove all of the hydrogen present in the feedstreams. Hence, each of these steps alone is inadequate to resolve the problems associated with the presence of hydrogen in the feedstream. As described above, further treatment by using silver oxide is therefore necessary.

In one embodiment of the invention, a gaseous mixture of olefins and hydrogen (the feedstream) is fed to the bottom of an absorption tower and a stream of silver nitrate is fed from the top enabling maximum contact time between the feed gases and silver nitrate so as to complex as much of the olefins in one pass as is possible. The complex formation and absorption of olefins by silver nitrate is a mildly exothermic process and thus the temperature of silver nitrate entering at the top of the absorption tower is usually lower than that of the same solution, now having complexed olefins therein.

The solution of the complex may suitably be withdrawn from the base of the absorption tower and pumped into a desorbing chamber where it is depressurised and heated to about 50 to 100° C., preferably, 60–90° C. The desorption process releases the complexed olefins from the silver nitrate solution and these are flashed off at the top of the desorption chamber. The olefins may be separated from one another, for example, by distillation. A suitable distillation method is described in WO 98/25871.

The residual (regenerated) silver nitrate solution is acidic, because the hydrogen present in the feedstream reacts with silver nitrate to produce nitric acid (see chemical equation I above). The reaction also converts at least some of the silver ions originally present in the silver nitrate solution to silver metal, reducing the capacity of the regenerated silver nitrate solution to complex with olefins. The silver metal may be entrained in the regenerated silver nitrate solution as a suspension of particulate silver, and this solution may optionally be passed through a filtering aid to remove particulate silver therefrom. The filtering aid may be located in the process stream either before or after the silver nitrate solution emergent from the desorption chamber is cooled to about 15–45° C., preferably, 20–40° C.

The particulate silver recovered from the filtering aid may be processed separately by converting back to a silver nitrate solution by dissolution thereof in a fresh aliquot of nitric acid.

The regenerated silver nitrate solution, whether filtered or not, is preferably cooled, and then passed through a bed of silver oxide to neutralise the excess acid and to replace the silver lost due to reduction by the presence of hydrogen. This step may be carried out at 10 to 50° C., preferably, 15 to 30° C., and 5 to 40 barg, preferably 7 to 24 barg.

The bed of silver oxide used is suitably in the form of pellets. Such pellets may be extruded without the use of a binding agent. Silver oxide may also be used in the form of a liquid (eg water) slurry, a dry powder or on an inert support such as a zeolite, an alumina or a clay. The silver oxide may be contacted with the regenerated silver nitrate solution in a stirred reactor or within a vessel. The vessel may be provided with an outlet filter to prevent the silver metal or silver oxide from exiting the vessel. The silver oxide enables control of the pH value of the silver nitrate solution within the region of 3 to 6, preferably, 3.5 to 5.5 and most preferably, 4 to 5.5. A surprising feature of the present invention is that the pH value of the silver nitrate solution is maintained within the desired region even when a large excess of silver oxide is present. This property of silver oxide is very important to the method of pH control chosen.

Thus, in summary, an embodiment of the process of the present invention may be carried out by bringing into contact a mixture of gases comprising the olefins with an aqueous solution of silver nitrate in a vertical absorption tower at about 7 to 24 barg and at about 15–30° C. A solution rich in the complex is separated from the non-absorbed gases by preferably, withdrawing the solution comprising the complex from the bottom of the absorption tower and feeding it into a lower pressure desorption vessel which is maintained at a relatively higher temperature (eg 60–90° C.). Here, the complex is broken down and the complexed olefin is released and recovered overhead. A lean, acidic solution of silver nitrate remains, and this is preferably cooled, optionally filtered, and neutralised by passing the solution through a bed of silver oxide. Thus treated, the solution is then recycled back to the absorption tower.

The benefits of the pH control process of the invention are that:
i) The olefin take up of the silver salt is not adversely affected—for every mole of silver deposited, a mole of acid is made, for every mole of acid neutralised, a mole of silver is solubilised.
ii) Corrosion of the materials of construction is controlled.
iii) The $NO_x$ levels in the product stream are controlled within the product specification.

The present invention is further illustrated with reference to the following Examples:

EXAMPLE 1

Ten batches of an aqueous solution containing silver nitrate (5 Molar) and silver acetylide (0.3% w/w) (initial solution "C") were tested by adding thereto aliquots of silver oxide. The initial solution (C) was acidic, having a pH of 1.12. the solution was then vigorously shaken, left overnight and filtered before measuring the pH thereof using a Metrohm double junction electrode. Silver oxide was added either in the form of a powder or as granules to solutions of silver nitrate/silver acetylide. The amounts used were calculated as follows:
i) Calculated amount (assuming 100% solubility) for neutralising a solution of silver nitrate having a pH value of 1.
ii) 10 times the amount of silver oxide calculated in (i) was added in the form of a powder to the silver nitrate/silver acetylide solution.
iii) The experiment in (ii) above was repeated except that the silver oxide was added in granular form.

The results of the experiments in (i) to (iii) above on the pH value of the resultant solutions are shown in the Table below:

| Ex | Amount and nature of silver oxide added | pH value |
|---|---|---|
| C | Initial solution of silver nitrate/silver acetylide | 1.12 |
| i) | Initial solution (C) + 0.116 g silver oxide (powder) | 3.85 |
| ii) | Initial solution (C) + 1.16 g silver oxide (powder) | 4.84 |
| iii) | Initial solution (C) + 1.16 g silver oxide (granules) | 3.99 |

EXAMPLE 2

10 ml of a 5 Molar solution of silver nitrate was used in this experiment with 1.16 g of silver oxide powder being added. The mixture was shaken occasionally over a 40 hour period, then filtered and the pH checked again as in Example 1 above. The pH value of the initial silver nitrate solution was 3.48 whereas that of the final solution was 5.29.

The above results show that silver oxide can be used to raise the pH value of the solution, with even the small quantities used in Example 1 (i) showing a marked effect. Addition of excess silver oxide only raised the pH value to about 5.3, showing that there is no risk of the pH rising too far, thereby enabling a slip stream solution comprising silver nitrate and silver acetylide to be passed through a bed of silver oxide to control the pH value of such a solution to a value of about 4.

EXAMPLE 3

The observation below shows that the pH of the silver nitrate solution drops on bubbling hydrogen; On bubbling a nitrogen feed containing 1000 ppm of hydrogen through a solution of silver nitrate, the pH value was seen to drop from 3.5 to 3.1 and traces of silver metal began to form.

EXAMPLE 4

Tests carried out by dissolving finely divided silver (prepared by bubbling hydrogen through silver nitrate) in various concentrations of nitric acid gave the following results:
40% v/v acid—Readily soluble
30% v/v acid—Soluble with agitation
20% v/v acid—Soluble with agitation over several minutes
A test with finely divided silver left in 20% nitric acid overnight showed that the silver had dissolved.
10% v/v acid—Soluble on standing for 48 hours.

What is claimed is:

1. A process for the pH control of a silver nitrate solution used for the selective recovery of olefins from a mixture of gases, said process comprising:

a) bringing a gaseous mixture comprising olefins and hydrogen into contact with an aqueous silver nitrate solution, whereby the olefins are absorbed into the silver nitrate solution as a complex;

b) separating the solution comprising the complexed olefins from the non-absorbed gases;

c) de-pressurising and heating the olefin complex solution from (b) so as to release the olefins from the complex and regenerate the silver nitrate solution;

d) passing said regenerated silver nitrate solution through a bed comprising silver oxide so as to maintain the pH value of the silver nitrate between 3 and 6; and e) recycling the silver nitrate solution regenerated in (d) to step (a).

2. A process as claimed in claim 1, wherein the silver oxide is used in granular form.

3. A process as claimed in claim 1, wherein the silver oxide is used in granular form in the absence of a binding agent.

4. A process as claimed in claim 1, wherein the silver oxide is used in powder form.

5. A process as claimed in claim 1, wherein the silver oxide is supported on a zeolite, a clay or an alumina.

6. A process as claimed in claim 1, wherein the silver nitrate solution employed in step (a) has a concentration of 1 to 10 M.

7. A process as claimed in claim 1, wherein an excess of silver oxide is employed in step (d).

8. A process as claimed in claim 1, which further comprises a step (f) of passing the silver nitrate solution regenerated in step (c) through a filtering aid, which is capable of retaining any particulate silver present in said regenerated silver nitrate solution.

9. A process as claimed in claim 8, wherein any particulate silver retained by said filtering aid is recovered and contacted with nitric acid to produce fresh silver nitrate.

10. A process as claimed in claim 8, wherein step (f) is carried out prior to step (d).

11. A process as claimed in claim 1, wherein acetylenic compounds are removed form the gaseous mixture comprising olefins and hydrogen.

12. A process as claimed in claim 11, wherein said acetylenic compounds are removed from said gaseous mixture before said gaseous mixture is contacted with silver nitrate solution in step (a).

13. A process as claimed in claim 11, wherein said acetylenic compounds are removed by passing the gaseous mixture through means capable of forming a complex with the acetylenic compounds in the gaseous mixture.

14. A process as claimed in claim 11, wherein said acetylenic compounds are removed by passing the gaseous mixture through a guard bed comprising a silver-ion exchanged zeolite.

15. A process as claimed in claim 1, which comprises:

monitoring an amount of acetylide compounds in the olefin complex solution formed in step (a) and removing at least a portion of said acetylide compounds from said solution before the amount of acetylide compounds is found to exceed to threshold level.

16. A process as claimed in claim 1, which is carried out for the selective recovery of ethylene and/or propylene from a petrochemical steam which has been subjected to steam cracking.

17. A process as claimed in claim 1, wherein the pH of the silver nitrate is maintained between 4 and 5.5.

\* \* \* \* \*

UNITED STATES PATENT AND TRADEMARK OFFICE
CERTIFICATE OF CORRECTION

PATENT NO.    : 6,491,888 B2
DATED         : December 10, 2002
INVENTOR(S)   : Peter Simpson Bell et al.

It is certified that error appears in the above-identified patent and that said Letters Patent is hereby corrected as shown below:

Column 7,
Line 2, "form" should read -- from --.

Column 8,
Line 6, "to threshold" should read -- a threshold --.
Line 9, "steam which" should read -- stream which --.

Signed and Sealed this

Sixth Day of May, 2003

JAMES E. ROGAN
*Director of the United States Patent and Trademark Office*